United States Patent
Thomas et al.

(10) Patent No.: US 8,846,359 B2
(45) Date of Patent: Sep. 30, 2014

(54) METHOD OF REGENERATING AN ENZYMATIC CATALYST

(71) Applicant: Total Raffinage Marketing, Puteaux (FR)

(72) Inventors: Daniel Thomas, Villers sur Coudun (FR); Sylviane Pulvin, Compiegne (FR); Lotfi Hedhli, Noisy le Roi (FR); Samuel Djelassi, La Chapelle Saint Luc (FR)

(73) Assignee: Total Marketing Services, Puteaux (FR)

( * ) Notice: Subject to any disclaimer, the term of this patent is extended or adjusted under 35 U.S.C. 154(b) by 0 days.

(21) Appl. No.: 13/623,374

(22) Filed: Sep. 20, 2012

(65) Prior Publication Data

US 2013/0078703 A1 Mar. 28, 2013

(30) Foreign Application Priority Data

Sep. 22, 2011 (FR) ...................................... 11 58470
Jan. 31, 2012 (FR) ...................................... 12 50923

(51) Int. Cl.
  *C12N 11/14* (2006.01)
  *C07K 14/805* (2006.01)
  *B01J 38/68* (2006.01)

(52) U.S. Cl.
  CPC .............. *C12N 11/14* (2013.01); *C07K 14/805* (2013.01); *B01J 38/68* (2013.01)
  USPC ........................................................ 435/176

(58) Field of Classification Search
  None
  See application file for complete search history.

(56) References Cited

U.S. PATENT DOCUMENTS

| 3,838,143 | A | * | 9/1974 | Grant ............................. 530/416 |
| 4,250,260 | A | * | 2/1981 | Rohrbach et al. ............. 435/176 |
| 4,683,203 | A | * | 7/1987 | Anton et al. ..................... 435/94 |
| 4,751,068 | A | * | 6/1988 | Bickar et al. ............... 423/437.2 |
| 4,971,904 | A | * | 11/1990 | Luddy ............................ 435/7.1 |
| 5,125,747 | A | * | 6/1992 | Sayegh et al. ................. 356/407 |
| 7,166,766 | B1 | | 1/2007 | Duhot et al. |
| 2012/0142983 | A1 | | 6/2012 | Vermeiren et al. |
| 2012/0157728 | A1 | | 6/2012 | Vermeiren et al. |

FOREIGN PATENT DOCUMENTS

WO    WO 2009/079688    7/2009

OTHER PUBLICATIONS

Brena, B.M., and Batista-Viera, F. In Methods in Biotechnology: Immobilization of Enzymes and Cells, 2nd Ed.; vol. 22, Guisan, J.M., Ed.; Humana Press Inc.: Totowa, New Jersey, 2006; pp. 15-30.*

* cited by examiner

*Primary Examiner* — Allison Ford
*Assistant Examiner* — Michelle F Paguio Frising
(74) *Attorney, Agent, or Firm* — Harness, Dickey & Pierce, P.L.C.

(57) ABSTRACT

A method of regenerating an enzymatic catalyst arranged in a reactor includes a mineral support based on metal oxide and at least one enzyme, wherein it contains at least one step of detachment of the spent enzymes by solvation by scavenging of the catalyst using at least one ionic surfactant, and at least one step of re-attachment of active enzymes by scavenging of the purified support with at least one solution of active enzymes, the two steps being performed in situ within the reactor.

14 Claims, 3 Drawing Sheets

METHOD OF REGENERATING AN ENZYMATIC CATALYST

CROSS-REFERENCE TO RELATED APPLICATIONS

This application claims the benefit and priority of French Patent Application Serial No. 1250923, filed on Jan. 31, 2012, and French Patent Application Serial No. 1158470, filed on Sep. 22, 2011, both of which are incorporated by reference herein.

BACKGROUND AND SUMMARY

The present invention relates to a method of regenerating an enzymatic catalyst by detachment/attachment of an enzyme on a support, said enzyme being used attached to its support in a catalytic reaction.

Nowadays more and more processes use enzymatic catalysis. In the vast majority of cases these processes require fixation of the enzyme on a particulate solid support, either for batch reactions, or for reactions with a fixed catalyst bed. However, enzyme lifetime is of limited duration and regeneration of catalysts containing enzymes is difficult compared to conventional catalysts. Catalyst regeneration consists of detaching the spent enzyme and then attaching an active enzyme on the support. This operation is often complicated, in particular on an industrial scale where large quantities of enzymes are used and their cost is reflected directly in the price of the manufactured products. In fact, until now, regeneration of an enzyme-based catalyst required emptying said catalyst from the reactors, treating the support of said catalyst to remove the spent enzyme, for example by chemical treatment and/or by calcination, then loading the support back in the reactor and finally attaching fresh active enzyme on the latter to restore the active catalyst. Such a method is laborious and expensive as it greatly increases reactor downtime.

The present invention aims to overcome these drawbacks by offering a method that does not require discharging the catalyst for replacing the enzyme, nor emptying the reactor containing it, which reduces reactor downtime. The present invention therefore relates to a method of regenerating an enzymatic catalyst arranged in a reactor comprising a mineral support based on at least one metal oxide and at least one enzyme, characterized in that it comprises at least one step of detachment of the enzymes from the support by solvation by scavenging the catalyst using at least one ionic surfactant until the spent enzymes have been removed, and at least one step of re-attachment of active enzymes by scavenging of said purified support with at least one solution of active enzymes, these two steps being performed in situ within the reactor.

This method not only gives a saving of time relative to the operations of handling and treatment of the support, but also a financial gain resulting from better optimization of the utilization of enzymatic catalysts. It offers the further advantage of being applicable to all types of supported enzymes and all applications using supported enzymes in reactions by enzymatic catalysis. By "enzyme" is meant a molecule allowing lowering of the activation energy of a reaction and acceleration of the chemical reactions taking place in the medium without altering the equilibrium that has been established. They also offer the advantage that they can be used at ambient temperature.

The step of detachment of the enzymes comprises scavenging the catalyst with an aqueous solution of so-called amphiphilic ionic surfactant, this surfactant being selected from the group consisting of salts of alkyl sulphonates, salts of alkyl sulphates, salts of alkyl sulphosuccinates, salts of alkyl phosphate esters, salts of alkylbenzene sulphonates, and quaternary ammonium salts, used alone or mixed. The ammonium salts are generally selected from the salts of formula N $R_1R_2R_3R_4^+$ in which $R_1$, $R_2$, $R_3$ and $R_4$ are alkyl, aryl, aralkyl or cycloalkyl groups comprising from 1 to 30 carbon atoms. Among the latter, the tetramethylammonium, tetraethylammonium, tetrapropylammonium, tetrabutylammonium, tetrapentylammonium, tetrahexylammonium, benzyltrimethylammonium, benzyltriethylammonium and hexamethionium salts are preferred. The phosphonium salts correspond structurally in all respects to the aforementioned ammonium salts.

During the step of detachment of the enzymes, the quantity of enzymes entrained in the effluent leaving the reactor will be measured by measuring, continuously or discontinuously, its absorbance at a wavelength characteristic of the sought enzyme by UV spectrometry. Typically, the wavelengths corresponding to the enzymes vary from 280 nm (nanometers) to 420 nm. In the case when the enzyme used is haemoglobin, the characteristic wavelength is 404 nm. The quantity of enzymes will decrease in the outgoing effluent as the detachment step proceeds. The concentration of spent enzymes measured by absorbance at a wavelength characteristic of the enzyme in UV spectrometry decreases in the outgoing effluent over the entire duration of said scavenging. The end of this step will be reached when the differential measurement of UV absorbance between the outgoing effluent and the stream entering the reactor becomes zero.

Among the ionic surfactants, the alkali metal and alkaline-earth metal salts of alkyl sulphates are preferred. They are selected from the salts of alkyl sulphates in which each alkyl group comprises from 6 to 20 carbon atoms in a linear or branched paraffinic chain, said chain preferably comprising from 10 to 16 carbon atoms. Preferably, the alkyl sulphate salt is a sodium salt of lauryl sulphate, also called sodium dodecyl sulphate (SDS). The ionic surfactant or surfactants are introduced into the reactor mixed with water, with a concentration preferably in the range from 1 to 50 g/L, more preferably from 1 to 20 g/L.

The method of the invention permits detachment of enzymes forming part of the group consisting of the six classes of enzymes, i.e. the hydrolases, the transferases, the oxidoreductases, the isomerases, the lyases or decarboxylases and the lycases. Among these enzymes, the method is particularly suitable for detachment of oxidoreductases, particularly haemoproteins and more particularly haemoglobin.

The supports allowing detachment and attachment of enzymes according to the method of the invention are preferably amorphous or crystalline mineral supports based on metal oxides selected from the group of crystalline, amorphous or composite materials comprising alumina, silica, zirconia, titanium dioxide or any composite material comprising at least one of these materials, with specific surface area in the range from 200 to 1000 m²/g, preferably from silica and/or alumina with specific surface area in the range from 200 to 600 m²/g. According to the method of the invention, re-attachment of the enzymes after the operation of detachment described above is obtained by scavenging the purified support with an enzyme solution until the concentration of enzyme, i.e. its absorbance measured at a wavelength characteristic of the required enzyme by UV spectrometry, increases in the outgoing effluent, and reaches the same absorbance as in the ingoing stream. The re-attachment step is carried out either immediately or later, with the same type of enzyme or a different type of enzyme.

The step of re-attachment of the enzymes is stopped when the differential measurement of the concentration of enzymes, expressed by their absorbance, measured in the ingoing stream and in the effluent leaving the reactor, becomes zero. In fact, the concentration of the solution of enzymes at the outlet is identical to that of the solution going into the reactor, i.e. they have an identical absorbance. If several enzymes of a different nature but mutually compatible were introduced onto the support, said enzymes being introduced together or sequentially, this would be within the scope of the invention.

In a preferred embodiment of the invention, the method includes, between the step of detachment of the spent enzymes and the step of attachment of the active enzymes, a step of washing the support in the reactor with water to remove the spent enzymes and especially the residual surfactant. During this washing step, the absorbance will be measured by UV spectrometry at the wavelength of SDS (260-280 nm) because it is preferable to remove all of the SDS used for detachment, prior to re-attachment of the enzymes. The differential measurement of absorbance between the outgoing effluent and the ingoing stream will remain high since surfactant alone or mixed with spent enzyme will be detected in the wash solution leaving said reactor. Accordingly, the washing step will come to an end when the differential measurement of absorbance between the two streams becomes zero, whether this relates to the UV absorbance of SDS or that of the enzymes that are detached.

According to one embodiment, the end of washing is reached when the absorbance at the wavelength characteristic of the enzyme in the outgoing effluent from the reactor becomes zero. After the re-attachment step, if we wish to use the regenerated enzymatic catalyst in an organic medium, it may be advantageous to circulate, in the reactor, a water/solvent mixture containing a gradually changing concentration from 100 to 0% of water for 0 to 100% of an organic solvent in said mixture, between the start and the end of drying, with drying corresponding to complete removal of water from the support, and optionally withdraw the surplus of unattached enzymes. This solvent will generally correspond to the solvents selected as reaction mixture, for example ketones, esters and ethers.

A second subject of the invention is the application of the method of the invention to all enzymatic catalysts in which the enzymes are attached to the support by low-energy bonds such as van der Waals bonds, electrostatic bonds or hydrogen bonds. A third subject of the invention is the use, in enzymatic catalysis, of the catalysts regenerated according to the method described above.

DRAWINGS

The drawings described herein are for illustrative purposes only of selected embodiments and not all possible implementations, and are not intended to limit the scope of the present disclosure.

DETAILED DESCRIPTION

The examples and figures given below aim to describe the invention in certain of its particular embodiments but are not to be regarded as limiting the scope thereof.

Example 1

In this example, a fresh enzymatic catalyst is prepared. A reactor is charged with 8.4 g of Davicat®SI 1700 silica (Merck), with specific surface area of 320 $m^2/g$, then a solution of unmodified haemoglobin (marketed by Vapran) at 10 g/l in a buffer solution at pH=5. An HPLC pump is adjusted to a flow of 1 ml/min in order to introduce the haemoglobin solution into the reactor and the timer is started at the moment when the first drop of haemoglobin enters the reactor.

Samples of the streams entering and leaving the reactor are taken regularly for measuring the concentration of haemoglobin, for determining by differential measurement between the ingoing stream and the outgoing effluent, the quantity of haemoglobin adsorbed by the silica. Thus, the absorbances of the ingoing stream and of the outgoing effluent are measured by UV spectrophotometry, using a UV UVIKON XS spectrometer marketed by Socoman, at 404 nm, the wavelength corresponding to that of haemoglobin. The difference in absorbance between the two streams is thus monitored as a function of the injection time.

Figure 1:
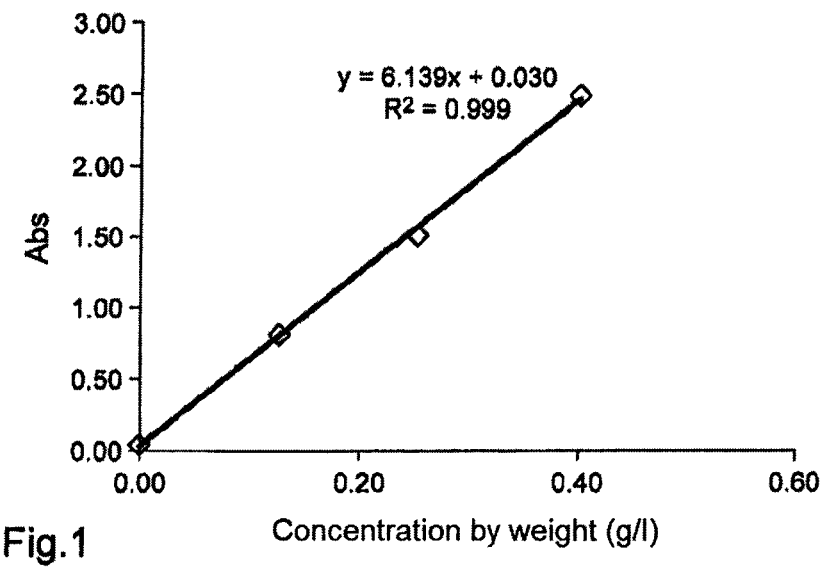
FIG. 1 is a calibration curve of UV absorbance at 404 nm as a function of concentration of haemoglobin in solution.

Of course, said UV spectrometer has been calibrated beforehand, using different standard solutions of haemoglobin in water at different concentrations. The calibration curve gives the measurement of UV absorbance as a function of haemoglobin concentration of the haemoglobin solution used for example for attachment (see FIG. 1, calibration curve of UV absorbance at 404 nm as a function of the concentration of the haemoglobin solution).

Figure 2:
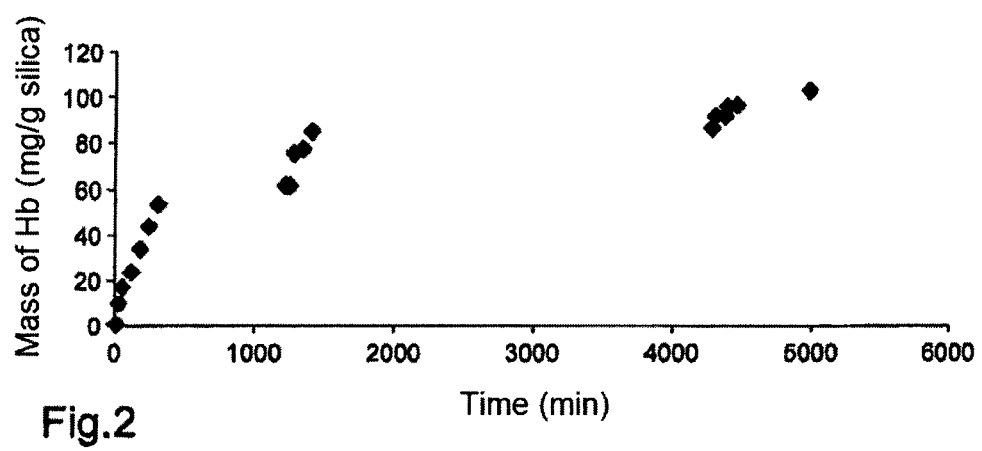
FIG. 2 is a curve showing mass of haemoglobin attached to silica, relative to mass of silica introduced in a reactor, as a function of time.

By calculating the quantity of haemoglobin introduced into the reactor before the differential measurement of absorbance between inlet and outlet becomes zero, it is possible to determine the maximum quantity of haemoglobin attached on the silica. FIG. 2 shows the variation of the quantity of haemoglobin that is attached to the silica, relative to the mass of silica introduced in the reactor. Saturation of the silica with haemoglobin is in this case 100 mg/g of silica. As haemoglobin is soluble in water up to a concentration of 100 g/l, it is possible to repeat this experiment at higher concentrations (for example 30 or 50 g/l) in order to reduce the time taken for attachment of the haemoglobin on the silica.

Example 2

This example describes the effect of the ingoing flow rate of the haemoglobin solution on the rate of attachment of the latter on the silica support for assessing the adsorption performance of the support for a fresh enzymatic catalyst. As in Example 1, the ingoing stream used is a haemoglobin solution at 10 g/l in water, which is percolated through the reactor packed beforehand with 8.4 g of Davicat®SI 1700 silica. The delivery of the HPLC pump is set to vary from 0.2 to 1 ml/min depending on the experiments (in FIG. 3; 0.2 ml/min; 0.5 ml/min; 1 ml/min), and for each of them, the timer is started at the moment when the first drop of haemoglobin solution enters the reactor.

Samples of the effluent at the reactor outlet are taken regularly in order to monitor the change in the haemoglobin concentration, and hence the quantity of haemoglobin that remained attached to the silica support relative to the quantity of haemoglobin in the stream entering the reactor. As before, the quantity of haemoglobin adsorbed on the silica is found from differential measurement between the absorbances of the ingoing stream, which are always constant, and those of the outgoing effluents as a function of the rate of injection of the haemoglobin solution.

Figure 3:
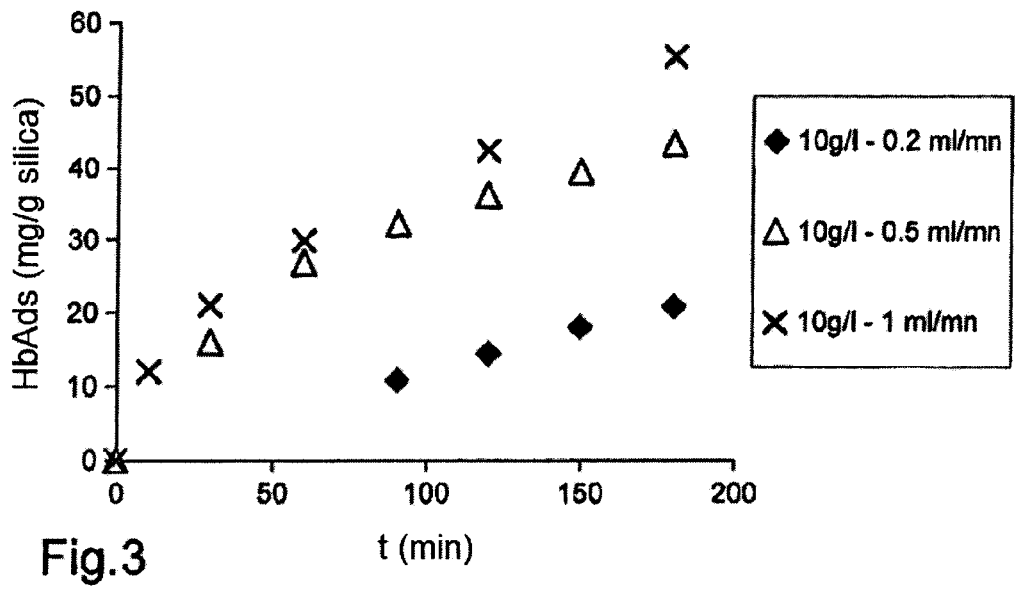
FIG. 3 are curves showing change in a quantity of haemoglobin attached per gram of silica as a function of time at various flow rates.

FIG. 3 shows the change in the quantity of haemoglobin attached per gram of silica, as a function of the flow rate of the feed pump for haemoglobin solution. It can be seen that the rate of adsorption of haemoglobin on the silica increases with increasing flow rate of the stream entering the reactor. The increase in flow rate makes it possible to reduce the time for saturation of the silica with haemoglobin.

Example 3

The present example describes the influence of the quantity of sodium lauryl sulphate (SDS) used in the step of detachment of the haemoglobin from the support as prepared in Example 1 on the absorbance measured in the haemoglobin solution, both at the reactor inlet and at the reactor outlet. In order to take account of the influence of the presence of SDS on the measurements of absorbance of the haemoglobin solution, measurements of absorbance were carried out with the UV spectrometer between 350-550 nm on solutions of haemoglobin with variable SDS contents, to calibrate the apparatus. These measurements were repeated for two haemoglobin concentrations at 0.25 g/l and at 50 g/l.

Figure 4:
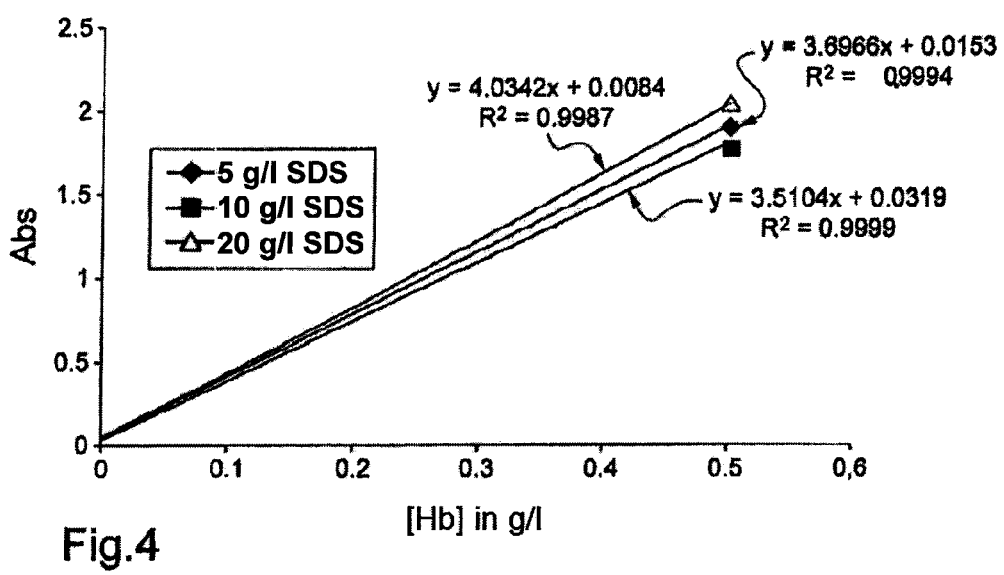
FIG. 4 are curves showing absorbance as a function of haemoglobin concentration for various concentrations of SDS.

FIG. 4 shows, regardless of the concentration of haemoglobin in the water in the ingoing stream, a decrease in UV absorbance characteristic of haemoglobin at 404 nm in the presence of SDS is noted. However, this change is stable over time. In fact, the concentration of SDS only has a very slight influence on the absorbance of haemoglobin at 404 nm, and moreover, linearity is well respected regardless of the concentration of SDS.

Example 4

The present example describes the step of detachment of the haemoglobin attached to silica in the case of the catalyst prepared in Example 2. Thus, we have an enzymatic catalyst containing 93 mg/g of haemoglobin absorbed on silica.

During the detachment step, an aqueous solution of SDS at 10 g/l is fed into the reactor at a flow rate of 1 ml/min by the HPLC pump described above. The quantity of haemoglobin detached from the silica is measured by comparing the absorbance values in the ingoing stream only containing SDS in solution and in the outgoing effluent still containing SDS but also haemoglobin. Calibration of the UV spectrometer was carried out as described in Example 1 with different standard solutions of haemoglobin in the presence of SDS. The calibration curves give the measurement of absorbance corresponding to the haemoglobin concentration of the standard solution (see FIG. 4).

Figure 6:
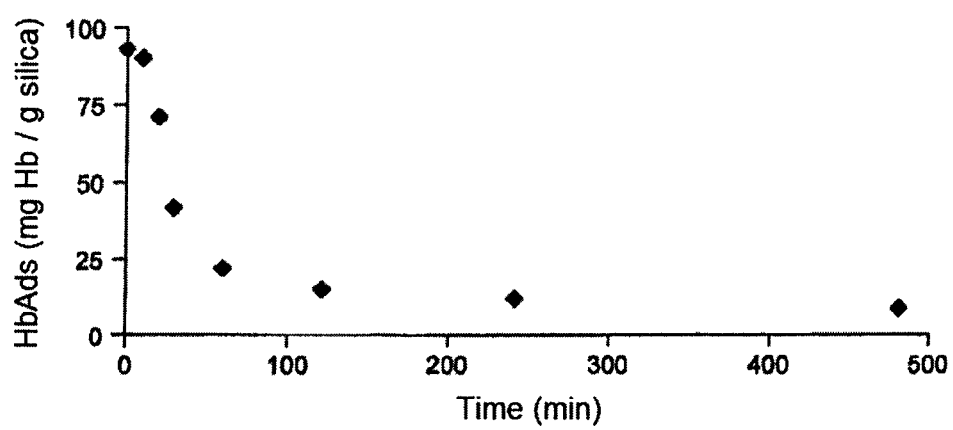
FIG. 6 is a detachment profile showing quantity of haemoglobin attached per gram of silica as a function of time.

Samples of the outgoing effluent are taken at 10 min, 20 min, 30 min, 60 min, 120 min, 240 min and 480 min in order to evaluate their absorbance at 404 nm and therefore their haemoglobin concentration at the reactor outlet. The haemoglobin desorption profile during the detachment phase is shown in FIG. 6 based on these measured values. At the end of this detachment step, 88 mg of haemoglobin/g of silica was detached and recovered at the reactor outlet, i.e. 95% of the quantity of haemoglobin initially absorbed on the silica.

Example 5

Figure 5:
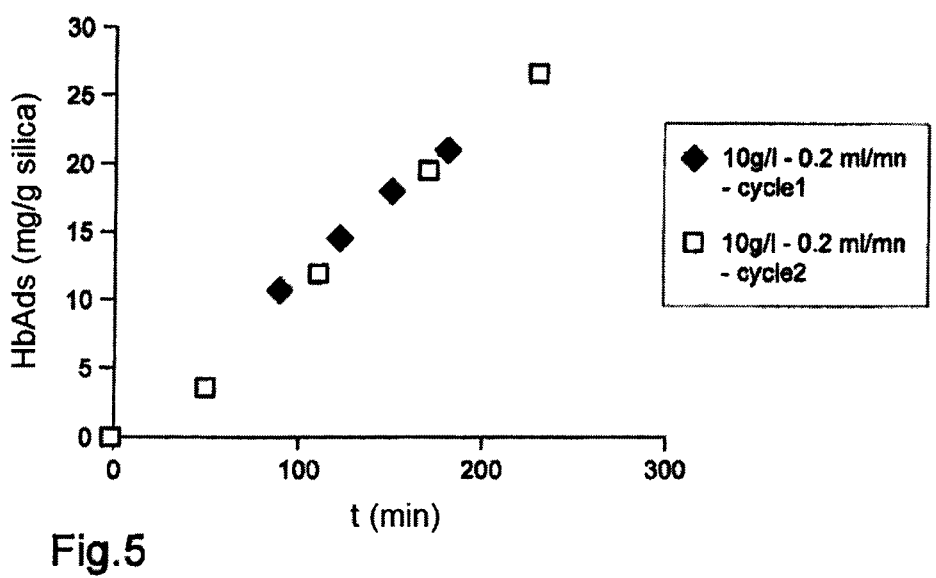
FIG. 5 are curves showing quantity of haemoglobin attached per gram of silica as a function of time for two cycles.

The present example describes the step of re-attachment of haemoglobin on the support from which the haemoglobin has just been detached according to Example 4, after a step of washing or rinsing of the reactor with water until SDS is no longer detected in the outgoing effluent from the reactor. At the end of this step, a haemoglobin solution at 10 g/l is reintroduced continuously, as described in Example 2, until the UV absorbance of the stream entering the reactor and of the effluent at the reactor outlet are identical, the haemoglobin content at the inlet and at the outlet being equal. The change in the quantity of haemoglobin fixed is presented in FIG. 5, showing the two cycles of attachment. Cycle 1 corresponds to attachment as described in Example 2 and cycle 2 corresponds to the re-attachment carried out after the steps of detachment and washing of the reactor described in the present example and in Example 4.

It can be seen that the corresponding immobilization profiles of the first cycle of attachment for preparing fresh catalyst and of the second cycle after detachment of the enzyme are superposed. Treatment with SDS for detachment of the haemoglobin from the silica therefore does not lead to a decrease in absorption potential of haemoglobin on silica, for the purpose of immobilization thereof.

The invention claimed is:

1. A method of regenerating a catalyst arranged in a reactor having a mineral support based on silica and hemoglobin, wherein saturation of the mineral support with hemoglobin is at least 100 mg of hemoglobin per gram of silica, said method comprising at least one step of detachment of the hemoglobin by solvation by scavenging of the catalyst using at least one ionic surfactant, and at least one step of re-attachment of active hemoglobin by scavenging of the purified support with at least one solution of active hemoglobin, these two steps being performed in situ within the reactor.

2. The method according to claim 1, wherein the step of detachment of the hemoglobin comprises scavenging of the catalyst with an aqueous solution of so-called amphiphilic ionic surfactant selected from the group including salts of alkyl sulphonates, salts of alkyl sulphates, salts of alkyl sulphosuccinates, salts of alkyl phosphate esters, salts of alkylbenzene sulphonates, and quaternary ammonium salts.

3. The method according to claim 1, wherein the concentration of spent hemoglobin measured by absorbance at a wavelength characteristic of the hemoglobin in UV spectrometry decreases in the outgoing effluent over the entire duration of the scavenging.

4. The method according to claim 1, wherein the end of the detachment step is reached when the differential measurement of the concentration of hemoglobin expressed by its absorbance between the outgoing effluent and the stream entering the reactor becomes zero.

5. The method according to claim 1, wherein among the ionic surfactants, the alkali metal salts of alkyl sulphates are selected from salts of alkyl sulphates, each alkyl group comprising from 6 to 20 carbon atoms in a linear or branched paraffinic chain.

6. The method according to claim 5, wherein the alkyl sulphate salt is a sodium salt of lauryl sulphate.

7. The method according to claim 1, wherein the steps of detachment and attachment of the hemoglobin are carried out on amorphous or crystalline silica with specific surface area in the range from 200 to 1000 m²/g.

8. The method according to claim 1, wherein the step of re-attachment of the hemoglobin is obtained by scavenging the purified support with a solution of hemoglobin until the concentration of hemoglobin, i.e. its absorbance at the characteristic wavelength, increases in the outgoing effluent.

9. The method according to claim 8, wherein the step of re-attachment of the hemoglobin is stopped when the differential measurement of the concentration of hemoglobin, measured in the ingoing stream and in the effluent leaving the reactor, becomes zero.

10. The method according to claim 1, further comprising, between the step of detachment of the spent hemoglobin and the step of attachment of the active hemoglobin, a step of washing the support in the reactor with water to remove the spent hemoglobin and especially the residual surfactant.

11. The method according to claim 10, wherein the end of washing is obtained when the absorbance at the characteristic wavelength of the hemoglobin in the outgoing effluent of the reactor becomes zero.

12. The method according to claim 1, further comprising regenerating all catalysts in which the hemoglobin is attached to the support by low-energy bonds.

13. The method according to claim 12, wherein the low-energy bonds are at least one of: van der Waals bonds, electrostatic bonds, or hydrogen bonds.

14. A method of regenerating and using a catalyst arranged in a reactor having a mineral support based on silica and hemoglobin, wherein saturation of the mineral support with hemoglobin is at least 100 mg of hemoglobin per gram of silica, said method comprising at least one step of detachment of the hemoglobin by solvation by scavenging of the catalyst using at least one ionic surfactant, and at least one step of re-attachment of active hemoglobin by scavenging of the purified support, these two steps being performed in in situ within the reactor, and using the catalysts in catalysis.

* * * * *